US006001134A

United States Patent [19]
Sørensen

[11] Patent Number: 6,001,134
[45] Date of Patent: Dec. 14, 1999

[54] OXIDATION ENZYME DERIVED FROM A STRAIN OF THE GENUS PYRICULARIA FOR THE OXIDATIVE DYEING OF KERATINOUS FIBERS

[75] Inventor: Niels Henrik Sørensen, Skævinge, Denmark

[73] Assignee: Novo Nordisk A/S, Bagsvaerd, Denmark

[21] Appl. No.: 09/158,934

[22] Filed: Sep. 22, 1998

Related U.S. Application Data

[63] Continuation of application No. PCT/DK97/00145, Apr. 3, 1997, abandoned.

[30]      Foreign Application Priority Data

Apr. 3, 1996 [DK] Denmark .................................. 0391/96

[51] Int. Cl.$^6$ ...................................................... A61K 7/13
[52] U.S. Cl. ........................... 8/401; 8/406; 8/408; 8/409; 8/410; 8/411; 8/412
[58] Field of Search ................................ 8/401, 406, 408, 8/409, 410, 411, 412, 416, 421, 423, 424, 649, 917; 435/41

[56]      References Cited

U.S. PATENT DOCUMENTS

| | | | |
|---|---|---|---|
| 3,251,742 | 5/1966 | Soloway | 8/401 |
| 5,667,531 | 9/1997 | Yaver et al. | 8/405 |

FOREIGN PATENT DOCUMENTS

| | | |
|---|---|---|
| 0 504 005 A1 | 9/1992 | European Pat. Off. . |
| 95/33836 | 12/1995 | WIPO . |
| 96/00290 | 1/1996 | WIPO . |

OTHER PUBLICATIONS

Chivukula et al., "Phenolic Azo Dye Oxidation By Laccese From *Pyricularia Oryzae*" Applied And Environmental Microbiology, Dec. 1995, pp. 4774–4377.

*Primary Examiner*—Caroline D. Liott
*Attorney, Agent, or Firm*—Steve T. Zelson, Esq.; Valeta Gregg, Esq.

[57]      ABSTRACT

Oxidation dyeing compositions for keratinous fibers which contain an oxidation enzyme derived from a strain of the genus Pyricularia, one or more dye precursors, and optionally, one or more modifiers, and methods for dyeing hair with such compositions.

14 Claims, 1 Drawing Sheet

OXIDATION ENZYME DERIVED FROM A STRAIN OF THE GENUS PYRICULARIA FOR THE OXIDATIVE DYEING OF KERATINOUS FIBERS

This application is a continuation of PCT/DK97/00145, filled Apr. 3, 1997, now abandoned.

FIELD OF THE INVENTION

The present invention relates to a dyeing composition for keratinous fibers, such as hair, a method for dyeing keratinous fibers and the use of an oxidation enzyme derived from Pyricularia for dyeing keratinous fibers, such as human or animal hair.

BACKGROUND OF THE INVENTION

It has been used for many years to dye the hair of humans to cover appearing grey hair. The need to do so arises from the fact that grey hair is the first sign of having past adolescence, which can be hard to accept for many people.

Further, during the last few decades hair dyeing has become more and more popular in the western world. At first Punk Rockers and other society critical groups dyed their hair in extreme colors as a part of their protest against the established society, but today especially many young people also use hair dyes (in more soft tints than the Punk Rockers) as a sort of "cosmetic" to change or freshen up their "looks".

Hair Dyes

In general hair dyeing compositions on the market today can be divided into three main groups:

temporary hair dyes, semi-permanent hair dyes, and permanent oxidative hair dyes.

The temporary hair dyes are only intended to change the natural hair color for a short period of time and usually function by depositing dyes on the surface of the hair. Such hair dyes are easy to remove with normal shampooing.

When using semi-permanent hair dyes the color of the dyed hair can survive for five or more shampooings. This is achieved by using dyes which have a high affinity for hair keratin and which are capable of penetrating into the interior of the hair shaft.

Permanent hair dyes are very durable to sunlight, shampooing and other hair treatments and need only to be refreshed once a month as new hair grows out. With such dyeing systems the dyes are created directly in and on the hair. Small aromatic colourless dye precursors (e.g. p-phenylenediamine and o-aminophenol) penetrate deep into the hair, where said dye precursors are oxidized by an oxidizing agent into coloured polymeric compounds. These coloured compounds are larger than the dye precursors and cannot be washed out of the hair.

By including compounds referred to as modifiers (or couplers) in the hair dyeing composition a number of hair color tints can be obtained. Cathecol and Resorcinol are examples of such modifiers.

Traditionally $H_2O_2$ is used as the oxidizing agent (color builder) . As $H_2O_2$ is also a bleaching agent dyeing compositions comprising $H_2O_2$ are often referred to as "lightening dyes".

The use of $H_2O_2$ in dye compositions has some disadvantages, as $H_2O_2$ damages the hair. Further, oxidative dyeing usually demands high pH (normally around pH 9–10), which inflicts damage on the hair and irritate the scalp. Consequently, when using dye compositions comprising $H_2O_2$, it is recommendable not to dye the hair often.

To overcome the disadvantages of using $H_2O_2$ it has been suggested to use oxidation enzymes to replace $H_2O_2$.

U.S. Pat. No. 3,251,742 (Revlon) describes a method for dyeing human hair by dye formation in situ (i.e. on the hair). An oxidative enzyme is used to the color formation reactions at a substantially neutral pH (pH 7–8.5). Laccases, tyrosinases, polyphenolases and catacolases are mentioned as the suitable oxidation enzymes.

EP patent no. 504.005 (Perma S.A.) concerns a composition for dyeing hair which do not require the presence of $H_2O_2$ (hydrogen peroxide). Said composition comprises an enzyme capable of catalyzing the formation of polymeric dyes, and also dye precursors, such as bases and couplers, in a buffer solution. The pH in said composition lies between 6.5 and 8 and said enzyme has an optimal activity in the pH range between 6.5 and 8.

*Rhizoctonia praticola* laccase and *Rhus vernicifera* laccase have a pH-optimum between 6.5 and 8 and can be used to form the polymeric dyes according to this patent.

WO 95/33836 (Novo Nordisk A/S) describes the use of a laccase derived from *Myceliopthora thermophila* which may be used for dyeing of hair.

WO 96/00290 (Novo Nordisk A/S) discloses the use of a laccase derived from *Polyporus pinsitus* for oxidative dyeing of hair.

It is known that *Pyricularia oryzae* laccase may be used oxidation of phenolic azo dyes (see Muralikrishna et al., (1995), Appl. Environ. Microbiol., 61, (12), pp. 4374–4377).

The use of Pyricularia laccase for dyeing keratinous materials such as hair is not mentioned and anticipated by said document.

SUMMARY OF THE INVENTION

The object of the present invention is to provide a permanent dyeing composition for keratinous fibers, such as hair, which has an improved color development (i.e. dyeing effect).

The terms "color development" and "dyeing effect" are used interchangeably in the following defining a color change (measured as DE) of the dyed keratinous fibre in question.

It has surprisingly been found that it is possible to provide such an improved hair dyeing composition by using a laccase derived from a strain of the filamentous fungus genus Pyricularia as the oxidation enzyme.

Firstly, the invention relates to a permanent dyeing composition for keratinous fibers, in particular hair, comprising an oxidation enzyme comprising 1) one or more oxidation enzymes derived from a strain of the genus Pyricularia,
2) one or more dye precursors, and optionally
3) one or more modifiers.

In a preferred embodiment of the invention the oxidation enzyme is a laccase derived from a strain of the genus Pyricularia, in particular from a strain of the species *Pyricularia oryzae.*

Secondly, it is the object of the invention to provide a method for dyeing keratinous fibers, in particular hair, comprising contacting an oxidative enzyme, such as a laccase, derived from a strain of the genus Pyricularia, in the presence or absence of at least one modifier, with at least one dye precursor, for a period of time, and under conditions sufficient to permit oxidation of the dye precursor.

Finally the invention relates to the use of an oxidation enzyme derived from a strain of the genus Pyricularia for oxidative dyeing of keratinous fibers, in particular hair.

DETAILED DESCRIPTION OF THE INVENTION

Figure 1:
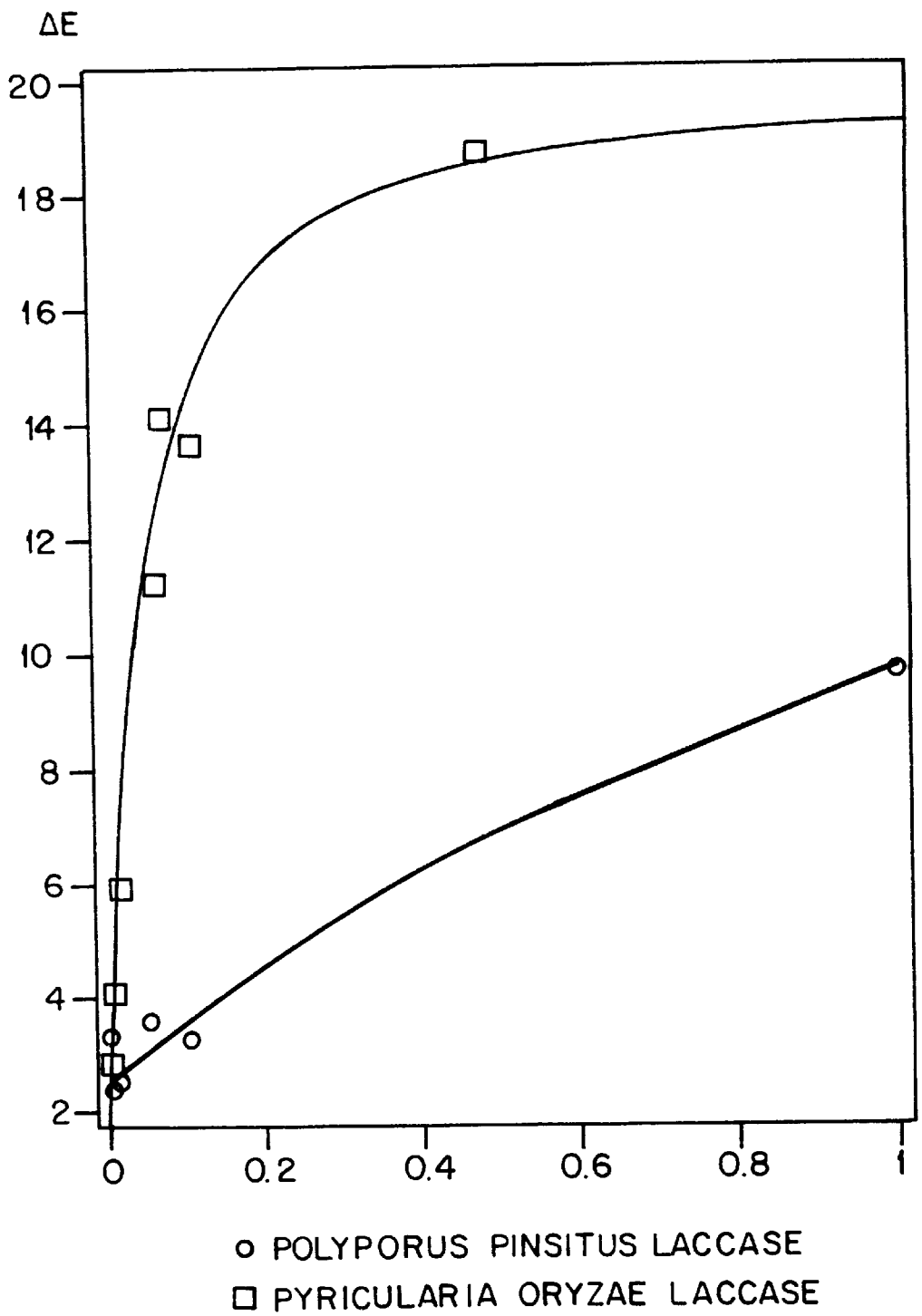
FIG. 1 shows the dose-response (i.e. ΔE vs. LACU/ml) for Pyricularia laccase and Polyporus lacase

The object of the present invention is to provide a permanent dyeing composition for keratinous fibers, such as hair, having improved dyeing effect.

It has surprisingly be found that it is possible to provide such an improved dyeing composition for keratinous fibers by using an oxidation enzyme derived from a strain of the filamentous fungus genus Pyricularia.

When using a fixed activity of laccase derived from a strain of the genus Pyricularia the color developed is improved when compared to the same activity of laccase derived from *Polyporus pinsitus* described in WO 96/00290 (Novo Nordisk A/S) (See Example 1).

Further, as shown in Example 2 the dose-response dyeing effect for Pyricularia laccase is higher than for Polyporus laccase.

Improved color development is, in the context of the present invention, defined as a DE higher than the DE value of the above mentioned *Polyporus pinsitus* laccase.

Consequently, in the first aspect the present invention relates to a permanent dye composition for keratinous fibers, such as hair, comprising 1) one or more oxidation enzymes derived from a strain of the genus Pyricularia,
2) one or more dye precursors, and
optionally 3) one or more modifiers.

In an embodiment of the invention the oxidation enzyme is a laccase derived from a strain of genus Pyricularia, such as a strain of *Pyricularia oryzae* e.g. the laccase which can be purchased from SIGMA under the trade name SIGMA no. L5510.

In addition, laccases derived from the genus Pyricularia also encompass alternative forms of laccases which may be found in Pyricularia as well as laccases which may be found in other fungi which are synonyms or fall within the definition of the genus Pyricularia.

It is to be understood that the Pyricularia laccases used for dyeing keratinous fibers according to the present invention may be produced homologously or heterologously using especially filamentous fungi, yeasts or bacteria as host cells.

Examples of filamentous fungus host cells include strains of the species of Trichoderma, preferably a strain of *Trichoderma harzianum* or *Trichoderma reesei*, or a species of Aspergillus, most preferably *Aspergillus oryzae* or *Aspergillus niger*, or yeast cells, such as e.g. a strain of Saccharomyces, in particular *Saccharomyces cerevisiae, Saccharomyces kluyveri* or *Saccharomyces uvarum*, a strain of Schizosaccharomyces sp., such as *Schizosaccharomyces pombe*, a strain of Hansenula sp., Pichia sp., Yarrowia sp., such as *Yarrowia lipolytica*, or Kluyveromyces sp., such as *Kluyveromyces lactis*, or a bacteria, such as gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of Streptomyces, such as *S. lividans* or *S. murinus*, or gram-negative bacteria such as *Escherichia coli.*

Laccases (benzenediol:oxygen oxidoreductases) (E.C. class 1.10.3.2 according to Enzyme Nomenclature (1992) Academic Press, Inc) are multi-copper containing enzymes that catalyze the oxidation of phenols. Laccase-mediated oxidations result in the production of aryloxy-radical intermediates from suitable phenolic substrates; the ultimate coupling of the intermediates so produced provides a combination of dimeric, oligomeric, and polymeric reaction products. Certain reaction products can be used to form dyes suitable for dyeing keratinous fibers such as hair (see below).

In an embodiment of the invention the Pyricularia laccase has improved color development properties at neutral pH. In the context of the present invention this means that the color development is improved when using the Pyricularia laccase in a dyeing composition having a pH in the range from between 5.0 and 9.0, in particular between 6.0 and 8.0, especially around pH 7.0.

To obtain a suitable dyeing of the keratinous fibers, such as hair, the dyeing composition of the invention must also comprise a dye precursor which is converted into a dye by the oxidation agent which according to the invention is an oxidation enzyme, especially a laccase, derived from a strain of the genus Pyricularia, such as a strain of species *Pyricularia oryzae*, especially the above mentioned laccase which can be purchased from SIGMA.

The dye precursor is preferably an aromatic compound e.g. belonging to one of three major chemical families: the diamines, aminophenols (or aminonaphtols) and the phenols.

Examples of such suitable dye precursors include p-phenylene-diamine (pPD), p-toluylene-diamine (pTD), chloro-p-phenylenediamine, p-aminophenol, o-aminophenol, 3,4-diaminotoluene, 2-methyl-1,4-diaminobenzene, 4-methyl-o-phenylenediamine, 2-methoxy-p-phenylenediamine, 2-chloro-1,4-diaminobenzene, 4-amino diphenylamine, 1-amino-4-β-methoxyethylamino-benzene, 1-amino-4-bis-(β-hydroxyethyl)-aminobenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-benzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, such as 4,7-phenazinedicarboxylic acid, 2,7-phenazinedicarboxylic acid, 2-phenazinecarboxylic acid, 2,7-diaminophenazine, 2,8-diaminophenazine, 2,7-diamino-3,8-dimethoxyphenazine, 2,7-diamino-3-methoxyphenazine, 2,7-diamino 3-methoxyphenazine, 3-dimethyl -2,8-phenazinediamine, 2,2'-[(8-amino-7-methyl-2-phenazinyl)imino]bis-ethanol, 2,2'-[(8-amino-7-methoxy-2-phenazinyl)imino]bis-ethanol, 2,2'-[(8-amino-7-chloro-2-phenazinyl)imino]bis-ethanol, 2-[(8-amino-7-methyl-2-phenazinyl)amino]-ethanol, 2,2'-[(8-amino-2-phenazinyl)imino]-bis-ethanol, 9-(diethylamino)-benzo[a]phenazine-1,5-diol, N-[8-(diethylamino)-2-phenazinyl]-methanesulfonamide, N-(8-methoxy-2-phenazinyl)-methanesulfonamide, N,N,N',N'-tetramethyl-2,7-phenazinediamine, and 3,7-dimethyl-2-phenazinamine, 3-amino-7-(dimethylamino)-2,8-dimethyl-5-phenyl-chloride, p-amino benzoic acids, such as p-amino benzoic acid ethyl, p-amino benzoic acid glycerid, p-amino benzoic acid isobutyl, p-dimethylamino benzoic acid amil, p-dimethylamino benzoic acid octyl, p-diethoxy amino benzoic amil, and p-dipropoxy amino benzoic acid ethyl, 2,3-diaminobenzoic acid, acetylsalicylic acid, and isatin derivatives.

In an embodiment of the invention the oxidative enzyme derived from Pyricularia is used with the dye precursor directly to oxidize it into a coloured compound.

It is to be understood that dye precursors can be used alone or in combination with other dye precursors. However, it is believed that at least one of the intermediates in the copolymerization must be an ortho- or para-diamine or aminophenol, such as p-phenylenediamine, o-aminophenol, p-methylaminophenol, p-aminophenol, p-toluylenediamine and N-phenyl-p-phenylenediamine. Contemplated are also all dye precursors listed in U.S. Pat. No. 3,251,742 (Revlon).

Optionally the hair dyeing composition of the invention also comprises a modifier (coupler) by which a number of hair color tints can be obtained. In general modifiers are used, as the hair colors resulting from hair dyeing compositions without modifier(s) are usually unacceptable to most people.

Modifiers are typically m-diamines, m-aminophenols, or polyphenols. The modifier (coupler) reacts with the dye precursor(s) in the presence of the oxidative enzyme, converting it into a coloured compound.

Examples of modifiers (couplers) include m-phenylenediamine, 2,4-diaminoanisole, 1-hydroxynaphthalene (α-naphthol), 1,4-dihydroxybenzene (hydroquinone), 1,5-dihydroxy-naphthalene, 1,2-dihydroxybenzene (pyrocatechol), 1,3-dihydro-xybenzene (resorcinol), 1,3-dihydroxy-2-methylbenzene, 1,3-dihydroxy-4-chlorobenzene (4-chlororesorcinol), 1,2,3-trihydroxybenzene, 1,2,4-trihydroxybenzene, 1,2,4-trihydroxy-5-methylbenzene, and 1,2,4-trihydroxytoluene.

In the second aspect the invention relates to a method for dyeing hair, comprising contacting an oxidation enzyme, such as a laccase, derived from a strain of the genus Pyricularia, in the presence or absence of at least one modifier, with at least one dye precursor, for a period of time, and under conditions sufficient to permit oxidation of the dye precursor.

The dyeing method can be conducted with one or more dye precursors, either alone or in combination with one or more modifiers. Amounts of components are in accordance with usual commercial amounts for similar components, and proportions of components may be varied accordingly.

When using an oxidation enzyme derived from Pyricularia, such as the *Pyricularia oryzae* laccase mentioned above, the method for dyeing hair of the invention may be carried out at room temperature and at a pH in the range from 5.0 to 9.0, preferably 6.0 to 8.0, especially around pH 7.

Suitable dye precursors and optionally modifiers are described above.

The use of an oxidative enzyme derived from Pyricularia, such as a laccase, is an improvement over the more traditional use of $H_2O_2$, in that the latter can damage the hair, and its use usually requires a high pH, which is also damaging to the hair. In contrast, the reaction with an enzyme can be conducted at acidic or neutral pH (below pH 9.0), and the oxygen needed for oxidation comes from the air, rather than via harsh chemical oxidation.

The result provided by the use of the oxidation enzyme derived from Pyricularia, such as a laccase, is comparable to that achieved with use of $H_2O_2$, not only in color development, but also in wash stability and light fastness. An additional commercial advantage is that a single container package can be made containing both the laccase and the precursor, in an oxygen free atmosphere, which arrangement is not possible with the use of $H_2O_2$.

Also when comparing the color development using an oxidation enzyme derived from the genus Pyricularia, such as a laccase, with a laccase such as the Polyporus laccase described above the Pyricularia oxidation enzyme gives improved color development.

MATERIALS AND METHODS

Materials
Hair: 6" De Meo Virgin Natural White Hair (De Meo Brothers Inc. U.S.)
Enzymes:
Laccase from *Pyricularia oryzae* purchased from SIGMA under the product name SIGMA no. L-5510, lot 54H3398, 389 UNITS/mg solid corresponding to 18.5 LACU/g.
Laccase from *Polyporus pinsitus* described in WO 96/00290, (103 LACU/ml).
Dye precursors:
0.1% w/w p-phenylene-diamine (pPD) in 0.1 M K-phosphate buffer, pH 7.0.
0.1% w/w o-aminophenol in 0.1 M K-phosphate buffer, pH 7.0.
Modifier:
0.1% w/w m-phenylenediamine in 0.1 M K-phosphate buffer, pH 7.0 .
Equipment:
Minolta CR200 Chroma Meter for color measurement Determination of Laccase Activity (LACU)

Laccase activity is determined from the oxidation of syringaldazin under aerobic conditions. The violet color produced is photometered at 530 nm. The analytical conditions are 19 mM syringaldazin, 23.2 mM acetate buffer, pH 5.5, 30° C., 1 minute reaction time.

1 laccase unit (LACU) is the amount of enzyme that catalyses the conversion of 1.0 mmole syringaldazin per minute at these conditions.

Assessment of the Hair Color

The quantitative color of the hair tresses are determined on a Minolta CR200 Chroma Meter by the use the parameters L* ("0"=black and "100"=white) , a* ("−60"=green and "+60"=red) and b* ("−60" blue and "+60" yellow).

DL*, Da* and Db* are the delta values of L*, a* and b* respectively compared to L*, a* and b* of untreated hair (e.g. $DL^* = L^*_{sample} - L^*_{untreated\ hair}$).

DE* is calculated as $DE^* = \ddot{O}(DL^{*2} + Da^{*2} + Db^*)$ and is an expression for the total quantitative color change (i.e. color development or dyeing effect).

EXAMPLES

Example 1
Dyeing Effect
The dyeing effect of a *Pyricularia oryzae* laccase was tested using the dye precursor p-phenylenediamine and compared with an equivalent activity of *Polyporus pinsitus* laccase under the same reaction conditions.
Hair Dyeing
1 gram De Meo white hair tresses were used.
4 ml dye precursor solution was mixed with 1 ml laccase on a Whirley mixer, applied to the hair tresses and incubated at 30° C. for 60 minutes. The activity of both the *Pyricularia oryzae* laccase and the *Polyporus pinsitus* laccase were 0.048 LACU/ml reaction mixture (pH 7).
The hair tresses were then rinsed with running water, washed with shampoo, rinsed with running water, combed, and air dried.

The a*, b* and L* was determined on the Chroma Meter and the DE* values were then calculated.

A hair tress sample treated without enzyme was used as a blind.

The result of the hair dyeing test is shown in the Table 1.

TABLE 1

|  | L* | DL | a* | Da* | b* | Db* | DE |
| --- | --- | --- | --- | --- | --- | --- | --- |
| Untreated hair | 73.4 | — | 2.4 | — | 23.7 | — | — |
| blind (without enzyme) | 66.7 | -6.7 | 4.2 | 1.8 | 23.2 | -0.5 | 7.0 |
| Polyporus laccase | 65.4 | -8.0 | 3.8 | 1.5 | 22.6 | -1.1 | 8.2 |
| Pyricularia laccase | 37.8 | -35.6 | 3.4 | 1.0 | 1.8 | -21.9 | 41.8 |

As can be seen from Table 1 the color development (i. e. DE) is improved when using the *Pyricularia oryzae* laccase for dyeing hair in comparison to a corresponding tests using the *Polyporus pinsitus* laccase.

Example 2

Dose-response dyeing test of *Pyricularia oryzae* laccase

The dyeing effect of from 0 to 1 LACU/ml *Pyricularia oryzae* laccase was compared with corresponding doses of *Polyporus pinsitus* laccase under the same conditions. 0.1% w/w o-aminophenol (dye precursor) and 0.1% w/w m-phenylene-diamine (modifier) was used.

Hair Dyeing 1 gram white De Meo hair tresses were used.

4 ml dye precursor solution (i. e. 2 ml dye precursor and 2 ml modifier) was mixed with 1 ml laccase in different concentrations (resulting in activities in the reaction mixtures from 0 to 1 LACU/ml) on a Whirley mixer, applied to the hair tresses in a glass beaker and incubated at 30° C. under shaking for 30 minutes.

The hair tresses were then rinsed with running water, washed with shampoo, rinsed with water, combed, and air dried.

a*, b* and L* were measured on the Chroma Meter and ΔE* was then calculated.

Hair tress samples treated without enzyme were used as blinds.

The result of the test is displayed in FIG. 1. From FIG. 1 it can be seen that the Pyricularia laccase gives a higher ΔE value than the Polyporus laccase at equivalent LACU/ml reaction mixture.

I claim:

1. A permanent dyeing composition for keratinous fibers, comprising:
   (a) one or more oxidation enzymes derived from a strain of the genus Pyricularia;
   (b) one or more dye precursors; and optionally
   (c) one or more modifiers.

2. The permanent dyeing composition of claim 1, wherein the oxidation enzyme is a laccase derived from a strain of the genus Pyricularia.

3. The permanent dyeing composition of claim 2, wherein the laccase is derived from a strain of the species *Pyricularia oryzae*.

4. The permanent dyeing composition of claim 1, having a pH in the range from 5.0 to 9.0.

5. The permanent dyeing composition of claim 4, having a pH of about 7.

6. The permanent dyeing composition of claim 1, wherein the dye precursor is selected from the group consisting of p-phenylene-diamine (pPD), p-toluylene-diamine (pTD), chloro-p-phenylenediamine, p-aminophenol, o-aminophenol, 3,4-diaminotoluene, 2-methyl-1,4-diaminobenzene, 4-methyl-o-phenylenediamine, 2-methoxy-p-phenylenediamine, 2-chloro-1,4-diaminobenzene, 4-amino diphenylamine, 1-amino-4-β-methoxyethylamino-benzene, 1-amino-4-bis-(β-hydroxyethyl)-aminobenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-benzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, 3-amino-7-(dimethylamino)-2,8-dimethyl-5-phenyl-chloride, p-amino benzoic acids, acetylsalicylic acid, and isatin derivatives.

7. The permanent hair dyeing composition of claim 1, wherein the modifier is selected from the group consisting of m-phenylene-diamine, 2,4-diaminoanisole, 1-hydroxynaphthalene, 1,4-dihydroxybenzene, 1,5-dihydroxynaphthalene, 1,2-dihydroxybenzene, 1,3-dihydroxybenzene, 1,3-dihydroxy-2-methylbenzene, 1,3-dihydroxy-4-chlorobenzene, 1,2,3-trihydroxybenzene, 1,2,4-trihydroxybenzene, 1,2,4-tri-hydroxy-5-methylbenzene, and 1,2,4-trihydroxytoluene.

8. A method for dyeing keratinous fibers, comprising contacting keratinous fibers to be dyed with an oxidation enzyme and at least one dye precursor, and optionally at least one modifier, wherein the oxidation enzyme is derived from a strain of the genus Pyricularia, wherein the fibers and enzyme are contacted for a period of time and under conditions sufficient to oxidize the dye precursor.

9. The method of claim 8, wherein the oxidation enzyme is a laccase derived from a strain of the genus Pyricularia.

10. The method of claim 9, wherein the laccase is derived from a strain of the species *Pyricularia oryzae*.

11. The method of claim 8, wherein the method is carried out at a pH in the range from 5.0 to 9.0.

12. The method of claim 11, wherein the pH is about 7.

13. The method according to claim 8, wherein the dye precursor is selected from the group consisting of p-phenylene-diamine (pPD), p-toluylene-diamine (pTD), chloro-p-phenylenediamine, p-aminophenol, o-aminophenol, 3,4-diaminotoluene, 2-methyl-1,4-diaminobenzene, 4-methyl-o-phenylenediamine, 2-methoxy-p-phenylenediamine, 2-chloro-1,4-diaminobenzene, 4-amino diphenylamine, 1-amino-4-β-methoxyethylamino-benzene, 1-amino-4-bis-(β-hydroxyethyl)-aminobenzene, 1-3-diamino-benzene, 2-methyl-1,3-diamino-benzene, 2,4-diaminotoluene, 2,6-diaminopyridine, 1-hydroxy-2-amino-benzene, 1-hydroxy-3-amino-benzene, 1-methyl-2-hydroxy-4-amino-benzene, 1-methyl-2-hydroxy-4-β-hydroxyethylamino-benzene, 1-hydroxy-4-amino-benzene, 1-hydroxy-4-methylamino-benzene, 1-methoxy-2,4-diamino-benzene, 1-ethoxy-2,3-diamino-benzene, 1-β-hydroxyethyloxy-2,4-diamino-benzene, phenazines, 3-amino-7-(dimethylamino)-2,8-dimethyl-5-phenyl-chloride, p-amino benzoic acids, acetylsalicylic acid, and isatin derivatives.

14. The method of claim 8, wherein the modifier is selected from the group consisting of m-phenylene-diamine, 2,4-diaminoanisole, 1-hydroxynaphthalene, 1,4-dihydroxybenzene, 1,5-dihydroxynaphthalene, 1,2-dihydroxybenzene, 1,3-dihydroxybenzene, 1,3-dihydroxy-2-methylbenzene, 1,3-dihydroxy-4-chlorobenzene, 1,2,3-trihydroxybenzene, 1,2,4-trihydroxybenzene, 1,2,4-trihydroxy-5-methylbenzene, and 1,2,4-trihydroxytoluene.

* * * * *